United States Patent [19]
Parent et al.

[11] Patent Number: 5,808,304
[45] Date of Patent: Sep. 15, 1998

[54] METHOD AND APPARATUS FOR DETECTING MALIGNANCIES IN LIVING TISSUE

[75] Inventors: Andre Parent, Quebec; Pierre Bernard, St-Augustin-de-Desmaures; Pierre Galarneau, Cap-Rouge, all of Canada

[73] Assignee: Aerospace Research Technologies, Inc., Ville St. Laurent, Canada

[21] Appl. No.: 746,944

[22] Filed: Nov. 18, 1996

[51] Int. Cl.⁶ .................................................. G01N 21/00
[52] U.S. Cl. ........................................ 250/341.1; 600/310
[58] Field of Search ................................ 250/341.1, 340, 250/358.1, 360.1; 128/664, 665; 600/310

[56] References Cited

U.S. PATENT DOCUMENTS 4,948,974  8/1990  Nelson et al. ........................ 250/358.1

OTHER PUBLICATIONS

Wist et al, Increased Spatial Resolution in Transillumenation Using Collimated light, IEEE Transactions on Medical Imaging vol. 12, No. 4, Dec. 1993 p. 751.

Primary Examiner—Michael J. Tokar
Assistant Examiner—Richard Hanig
Attorney, Agent, or Firm—George A. Seaby

[57] ABSTRACT

The most common method of determining whether a breast contains cancerous tissue utilizes ionizing radiation, i.e. x-rays, which possible have tissue damaging properties. It has been found that lasers can be used as a light source in a breast tissue transillumination process. However, due to the high scattering coefficient (or diffusing properties) of breast tissue, it is not possible to obtain images having good resolution using classical transillumination techniques, even when a laser is used as the light source. When passing through a diffusing medium, a laser pulse decomposes into three classes of photons, namely ballistic, snake-like and diffuse photons. In most practical situations, the ballistic photon portion of a laser pulse, which travels in a straight line, does not pass through the tissue, i.e. only snake-like and diffuse photons pass through the tissue. It is proposed by this invention to use both the snake-like and diffuse photons in a method involving time gating and multiple field of view techniques to obtain a more precise evaluation of the scattering coefficients, i.e. a map of the interior of a region of the sample, whereby the presence (or absence) of tumors is determined. The use of multiple field of view and time gating techniques will yield a relatively clear picture of the structure of the tissue.

10 Claims, 3 Drawing Sheets

METHOD AND APPARATUS FOR DETECTING MALIGNANCIES IN LIVING TISSUE

BACKGROUND OF THE INVENTION

1. Field of the Invention

This invention relates to a method and an apparatus for detecting malignancies in living, biological tissue, and in particular to a method and apparatus for detecting breast cancer.

2. Discussion Of The Prior Art

As described fully in the preamble to U.S. Pat. No. 5,371,368, which issued to Robert R. Alfano et al on Dec.6, 1994, breast cancer has the highest incidence rate and the highest mortality rate of any cancer in the United States. In fact, breast cancer, which affects more than eight percent of women, is the most deadly disease amongst this segment of our population. At present, early detection and treatment are the best hopes for reducing the death rate due to this terrible disease. Considerable efforts have been made to improve upon existing detection systems. In general, existing screening methods rely on x-ray mammography, which gives rise to a concern about the possibility of developing cancer as a result of irradiation using x-rays. The use of ultrasound has also been proposed; however, ultrasonic techniques also have documented drawbacks.

Recent research has resulted in methods and apparatus for detecting breast cancer using non-ionizing radiation, e.g. visible or non-visible light. Canadian Patent No. 1,149,631, which issued to Robert G. Carroll on Jul. 12, 1983 is a basic source of information concerning the concept of non-invasive examination of living human tissue using non-ionizing radiation. Other literature relating to developments in breast cancer detection involving trans,illumination of the breast is listed at the top of the second column of the above referenced Alfano et al U.S. patent.

GENERAL DESCRIPTION OF THE INVENTION

In spite of the advances made in the detection of breast cancer using non-ionizing radiation, a need still exists for a method and apparatus or system which results in clear images.

An object of the present invention is to meet the above need by providing a relatively simple method and apparatus for detecting breast cancer using non-ionizing radiation, namely laser pulses for transillumination of a breast.

Another object of the invention is to provide a method and apparatus of the above-defined type which results in relatively clear images, facilitating the detection of breast cancer. By "images" is meant maps of the scattering properties of breast tissue where it is believed that malignancies have different scattering properties than normal tissue.

Thus, according to one aspect the invention relates to a method of detecting the presence of a malignant mass in a living tissue sample comprising the steps of:

(a) applying an ultrafast laser pulse to the living tissue sample;

(b) defining a region of light passing through the tissue sample; and (c) utilizing multiple field of view and time gating techniques to determine the scattering coefficients of the tissue sample, whereby a mapping of the scattering properties and consequently the presence of any malignant mass in the tissue sample is determined.

According to another aspect, the invention relates to an apparatus for detecting the presence of a malignant mass in a living tissue sample comprising:

(a) laser means for producing an ultrafast laser pulse;

(b) holder means transparent to said laser pulse for holding the tissue sample while the laser pulse passes therethrough;

(c) multiple field of view separator means for simultaneous spatial separation of light coming into different fields of view and for effecting temporal dispersion of the laser pulse exiting the tissue sample; and (d) detector means for temporally resolving the laser pulse exiting the tissue sample for detecting said different fields of view from said separator means to provide primary data for processing to produce a clear image of the interior of the tissue sample.

BRIEF DESCRIPTION OF THE DRAWINGS

The invention is described hereinafter in greater detail with reference to the accompanying drawings, which illustrate a preferred embodiment of the invention, and wherein.

DESCRIPTION OF THE PREFERRED EMBODIMENT

Figure 1:
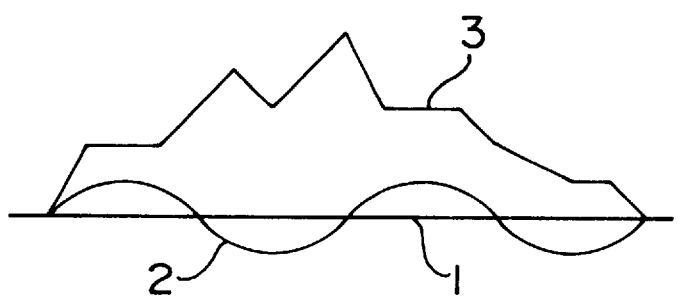
FIG. 1 is a schematic representation of signals of a laser pulse propagating through a diffusing medium.

Referring to FIG. 1, when an ultrafast laser pulse, for example a laser pulse with a temporal length of less than a few picoseconds, propagates through a diffusing medium such as a breast. The light is scattered and decomposes into three classes of photons, namely ballistic, snake-like and diffused photons. Ballistic photons take a straight line path of travel 1 through the diffusing medium without being deviated by the medium. Images formed by such photons show maximum contrast and resolution. Snake-like photons are scattered slightly by the diffusing medium, and therefore take an approximately straight line path of travel 2 through the medium. The snake-like photons zig-zag around a straight line path of travel 1. Images formed by snake-like photons have lower contrast and resolution than ballistic photons. Diffused photons are subject to substantial scattering, taking an erratic path of travel 3 through the medium, and the images formed by such photons are completely blurred.

Obviously, the best image resolution is provided by ballistic photons. However, in most practical applications, the diffusion through biological tissue is too high and no ballistic photons are transmitted, i.e. only snake-like and diffused photons pass through the tissue. Recent experiments suggest that it is possible to form good resolution images using snake-like photons only. Since in biological tissue for the present applications and for the region of wavelength of interest, i.e. between 600 and 1500 nm, the absorption of photons during propagation is not the dominant factor, the properties of transmitted photons will be dictated mainly by the diffusing properties of the tissue. It is believed that abnormal tissue has optical properties (mainly the scattering coefficient) which differ from those of normal tissue. The concept of imaging through biological tissue with an ultrafast laser is based on the difference in scattering coefficients.

In order to retrieve the information carried by snake-like photons, the latter must be separated from the diffuse photons. Since snake-like photons follow a straighter path of travel 2 than diffuse photons, they take less time to travel through the tissue and will arrive first at the side of the tissue opposite to the side to which the laser pulse is applied. The present inventors use this temporal dispersion to selectively retrieve the information imparted by snake-like photons. By using time-gating techniques it. is possible to retrieve image information from the snake-like photons deleting the background from diffuse photons. The population of transmitted snake-like photons from a laser pulse passing through a tissue sample will be different for regions with different scattering coefficients. In other words, by measuring variations of the population of transmitted snake-like photons in a given time period or gate, it is possible to obtain an image of the distribution of the scattering coefficients, and consequently to map the interior of the tissue sample, whereby the presence (or absence) of abnormalities or tumors is determined.

Moreover, rather than disregarding the diffuse photons as others such as Alfano et al (supra) have done, the present inventors use such photons to obtain a more precise evaluation of the scattering coefficient of a scanned region of a tissue sample, and consequently a better image.

Figure 2:
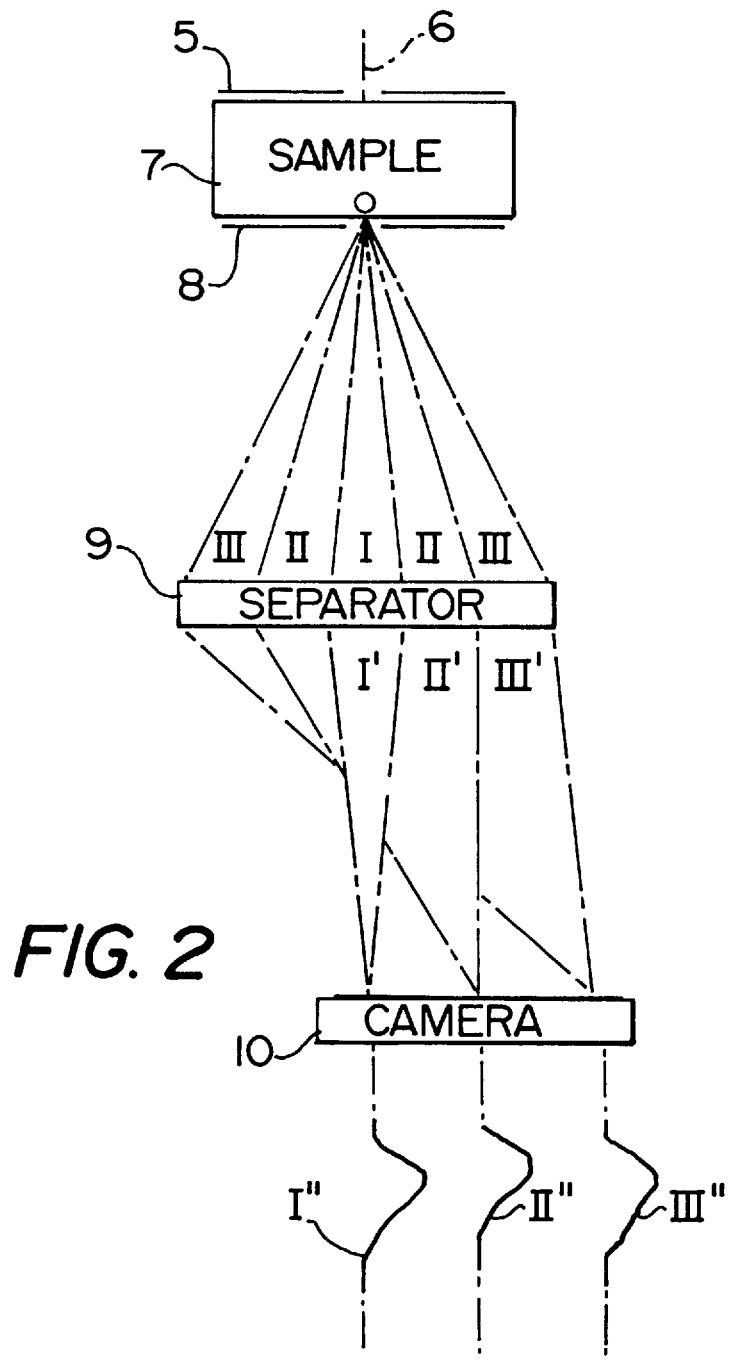
FIG. 2 is a schematic diagram of a multiple field of view system for use in the apparatus of the present invention.

The multiple field of view system used to characterize the diffusing or scattering properties of the breast tissue is illustrated in FIG. 2. A system of this type is described in U.S. Pat. No. 5,239,352, which issued to Luc R. Bissonnette on Aug. 24, 1993. Basically, the system includes an input aperture 5 for precisely defining the size of an input beam or laser pulse 6 entering a tissue sample 7. Light passing through the tissue sample 7 passes through an output aperture 8 which has a fixed or variable diameter for defining the scanned region. The light exiting the aperture 8 is scattered into separate field of view or cones I, II and III, which have different emergent angles. Of course, the number of fields of view is not limited to three, the number shown being used for the purpose of illustration only. The cones I, II and III pass through a multiple field of view separator 9 which simultaneously separates the cones of light received form the sample 7, and separates the light into different, discrete fields of view or cones I', II' and III', i.e. at different angles depending upon the nature of the photons. The multiple scattered light enters a detector defined by a streak camera 10 which produces a streak image. The camera 10 provides laser outputs in the different fields of view I", II" and III".

Basically, the multiple field of view system effects spatial separation of light emanating from the sample, and redirects the light into different fields of view, i.e. at different angles. The contributions for the different fields of view provide additional information and provide all that is necessary to determine the scattering coefficients $\mu_s$ of the medium. The reduced scattering coefficients $\mu_s'$ of a tissue sample is given by $$\mu_s'=\mu_s(1-g)$$

where $\mu_s$ is the scattering coefficient and g is the mean cosine of the scattering angle. By looking simultaneously at the light diffusing from the media at different angles instead of merely examining the axis, the present inventors are able to more precisely determine the scattering properties of the medium. Such precise determination is possible using the multiple field of vision system described herein.

Figure 3:
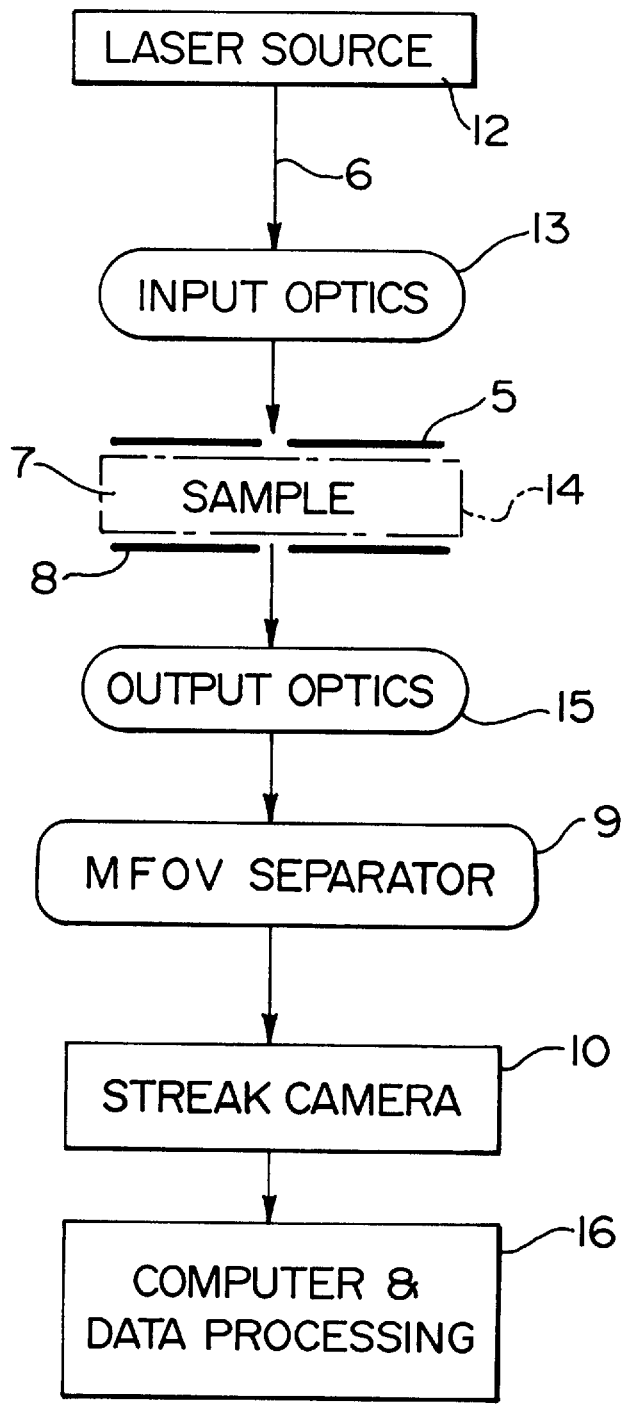
FIG. 3 is a schematic block diagram of a breast imaging apparatus in accordance with the present invention.

Referring to FIG. 3, in addition to the elements described above, the apparatus for carrying out the method of the present invention includes a laser source 12 for generating an ultrafast laser pulse 6 with emission wavelengths from 600 to 1500 nm, a temporal pulse length of 100 femtoseconds to 50 picoseconds and a pulse repetition rate of 60 to 120 kilohertz. A suitable laser source 12 is a modelocked titanium:sapphire laser pumped by an argon laser, a modelocked titanium:sapphire laser pumped by a frequency doubled Nd:YAG laser, a modelocked titanium:sapphire laser pumped by a frequency doubled ND:YLF laser, a modelocked diode laser, a modelocked Forsterite laser or a modelocked Cr:YAG laser. A modelocked laser generally has a pulse repetition of 60 to 120 Mkz. The laser pulse 6 passes through input optics 13 defined by lenses, holographic elements, binary optics or an apodizer in order to modify the input laser pulse 6 to match the particular requirements of the tissue being investigated. After passing through the input optics 13, the pulse 6 passes through the input aperture 5 to the tissue sample 7, which is mounted in a holder 14. The holder 14 is transparent to the pulse 6, and which effects a small compression of the breast to cause the tissue under investigation to assume a uniform thickness. Upon exiting the sample 7, the beam passes through the output aperture 8 and output optics 15 to the holographic separator 9. The output optics 15 are defined by a lens, holographic elements, binary optics or an apodizer for modifying the parameters of the output beam in accordance with the character of the sample 7 being analyzed. The beam then enters the multiple field of view separator 9 for spatial separation of the light from the sample 7, and the scattering of such light into the different fields of view. The beam then passes to the streak camera 10, which yields results, which are fed to computer and data processing equipment 16. The equipment 16 produces an image of the area of tissue under examination.

We claim:

1. A method of detecting the presence of a malignant mass in a living tissue sample comprising the steps of:
    (a) applying an ultratast laser pulse to the living tissue sample;
    (b) simultaneously spatially separating light passing through the tissue sample and redirecting the light into different fields of view;
    (c) temporally resolving the light in said fields of view to provide primary data; and
    (d) processing said data to map the scattering properties and consequently the presence of any malignant mass in the tissue sample.

2. A method according to claim 1, wherein the laser pulse has an emission wavelength of from 600 to 1500 nm, a temporal pulse length of 100 femtoseconds to 50 picoseconds, and a pulse repetition rate of 60 to 120 Mkz.

3. A method according to claim 2, wherein the laser beam is modified before reaching the tissue sample to precisely define the size of and the divergence an input laser beam and consequently the region of the tissue sample scanned.

4. A method according to claim 3, wherein the tissue is compressed on a tissue holder transparent to the laser pulse to make the tissue sample thickness uniform in the scanned region.

5. A method according to claim 4, wherein light output from the tissue sample is focussed to precisely define the scanned region.

6. An apparatus for detecting the presence of a malignant mass in a living tissue sample comprising:
    (a) laser means for producing an ultrafast laser pulse;
    (b) holder means transparent to said pulse for holding the tissue sample while the laser pulse passes therethrough (c) separator means for simultaneously spatially separating the light passing through the sample and redirecting the light into different fields of view.

(d) detector means for temporally resolving light from said different fields of view to provide primary data for processing to produce a clear image of the interior of the tissue sample.

7. An apparatus according to claim 6, wherein said laser means is a laser source capable of generating a laser pulse having an emission wavelength of from 600 to 1500 mn, a temporal pulse length of 100 femtoseconds to 50 picoseconds, and a pulse repetition rate of 60 to 120 Mkz.

8. An apparatus according to claim 7, including input optical means and input aperture for modifying the ultrafast laser pulse before passage of said pulse into the tissue sample.

9. An apparatus according to claim 8, including output optical means for modifying an output beam from the tissue sample in accordance with the diffusing properties of the sample being analyzed.

10. An apparatus according to claim 9, wherein said detector means includes streak camera means for receiving the modified beam from said output optical means.

* * * * *